United States Patent
Doerr et al.

(10) Patent No.: US 9,827,414 B2
(45) Date of Patent: Nov. 28, 2017

(54) MEDICAL IMPLANT WITH A FIXING DEVICE

(71) Applicant: Biotronik SE & Co. KG, Berlin (DE)

(72) Inventors: Thomas Doerr, Berlin (DE); Michael Diebold, Berlin (DE)

(73) Assignee: BIOTRONIK SE & CO. KG, Berlin (DE)

( * ) Notice: Subject to any disclaimer, the term of this patent is extended or adjusted under 35 U.S.C. 154(b) by 30 days.

(21) Appl. No.: 14/803,003

(22) Filed: Jul. 17, 2015

(65) Prior Publication Data

US 2016/0051811 A1   Feb. 25, 2016

Related U.S. Application Data

(60) Provisional application No. 62/039,931, filed on Aug. 21, 2014.

(51) Int. Cl.
*A61N 1/05*       (2006.01)
*A61B 17/064*   (2006.01)

(52) U.S. Cl.
CPC ............ *A61N 1/059* (2013.01); *A61B 17/064* (2013.01); *A61B 17/0643* (2013.01); *A61N 1/05* (2013.01); *A61N 1/057* (2013.01); *A61B 2017/0649* (2013.01)

(58) Field of Classification Search
CPC .......... A61N 1/059; A61N 1/057; A61N 1/05; A61B 2017/0649; A61B 17/064; A61B 17/0643

See application file for complete search history.

(56) References Cited

U.S. PATENT DOCUMENTS

| 6,981,983 | B1 * | 1/2006 | Rosenblatt ......... A61B 17/0401 128/898 |
| 6,986,784 | B1 | 1/2006 | Weiser et al. |
| 8,244,377 | B1 * | 8/2012 | Pianca .................. A61N 1/057 607/116 |
| 2002/0013605 | A1 * | 1/2002 | Bolduc ................ A61B 17/064 606/213 |
| 2002/0103521 | A1 | 8/2002 | Swoyer et al. |
| 2002/0165589 | A1 | 11/2002 | Imran et al. |
| 2008/0109054 | A1 * | 5/2008 | Hastings .............. A61N 1/0587 607/127 |
| 2009/0204170 | A1 | 8/2009 | Hastings et al. |
| 2012/0245663 | A1 | 9/2012 | Zarembo et al. |
| 2014/0148849 | A1 | 5/2014 | Serina et al. |

OTHER PUBLICATIONS

European Search Report received from EP Application Serial No. 15167567, dated Jan. 4, 2016, 8 pages.

* cited by examiner

*Primary Examiner* — Anh Dang
(74) *Attorney, Agent, or Firm* — Arc IP Law, PC; Joseph J. Mayo

(57) ABSTRACT

Embodiments include a medical implant for insertion into the human and/or animal body. The medical implant includes a helical fixing device to fix the implant at a site of implantation, wherein the helical fixing device is one or more of coupled to a locking device on the fixing device and coupled to an implant surface. One or more of the locking device and the implant surface impedes an autonomous detachment of the fixing device.

13 Claims, 4 Drawing Sheets

MEDICAL IMPLANT WITH A FIXING DEVICE

This application claims the benefit of U.S. Provisional Patent Application 62/039,931 filed on 21 Aug. 2014, the specification of which is hereby incorporated herein by reference.

BACKGROUND OF THE INVENTION

Field of the Invention

Embodiments of the invention generally relate to a medical implant with a fixing device for insertion into the human and/or animal body.

Description of the Related Art

Generally, it is known to fix medical implants at the site of implantation by means of fixing devices. Typically, helical fixing devices are used inter alia, in which a helix is screwed into the tissue and anchors the implant to the tissue. In order to prevent the helix from automatically unscrewing, generally, the helices are fixed by the surgeon by means of one or more sutures. Typically, this presupposes that the site of implantation is sufficiently accessible.

BRIEF SUMMARY OF THE INVENTION

One or more embodiments of the invention provide a medical implant including a helical fixing device that may be securely fixed, even at sites of implantation that are difficult to access.

One or more embodiments of the invention are achieved in accordance with the elements of the independent claims. Embodiments of the invention will emerge from the other claims, the description and the drawings presented herein.

At least one embodiment of the invention includes a medical implant that is inserted into the human and/or animal body. In one or more embodiments, the medical implant includes a helical fixing device to fix the implant at a site of implantation. In at least one embodiment, the helical fixing device may be coupled to a locking device on the helical fixing device and/or may be coupled to an implant surface, wherein one or more of the locking device and the implant surface at least impedes an autonomous detachment of the helical fixing device.

In at least one embodiment of the invention, dislocation of an implant fixed only by a helix may be prevented using the locking device. As such, in one or more embodiments, the implant may be positioned even at points that may only be accessed with difficulty, rendering many sites of implantation accessible, that previously would have to be ruled out using typical devices. At least one embodiment of the invention includes positioning of the implantable device, such as an epicardial pacemaker, which may be inserted deep between the myocardium and pericardium. In one or more embodiments, the spatial requirement of the locking device is low, such that the positioned implant requires little space.

In at least one embodiment, the locking device may include one or more barbs on the fixing device. In one or more embodiments, the one or more barbs may already protrude from the helix during the positioning of the helix, wherein the one or more barbs are directed such that a screwing of the helix into the tissue is not hindered, however an unscrewing is impeded. In one or more embodiments, the one or more barbs may penetrate the tissue only when the helix has been screwed in. As such, at least one embodiment may allow repositioning of the implant, wherein the helix may first be unscrewed again from the tissue.

In one or more embodiments, the locking device may include one or more barbs on the implant surface. In at least one embodiment, the one or more barbs may already protrude from the helix during the positioning of the helix, wherein the barbs are directed such that a screwing of the helix into the tissue is not hindered, however an unscrewing is impeded. In one or more embodiments, the one or more barbs may penetrate the tissue only when the helix has been screwed in. As such, at least one embodiment may allow repositioning of the implant, wherein the helix may first be unscrewed again from the tissue.

One or more embodiments of the invention may include a combination of the one or more barbs on both the fixing device and on the implant surface.

In at least one embodiment, at least one barb may be covered temporarily with a resorbable coating, wherein the resorbable coating may expose the at least one barb in order to fix the implant at the site of implantation. In one or more embodiments, the at least one barb may include a spring force, wherein the resorbable coating fixes the at least one barb on the fixing device and/or on the implant surface, against the spring force of the at least one barb. As such, at least one embodiment of the invention may allow simple repositioning of the implant, wherein the helical fixing device may be screwed repeatedly into the tissue and removed therefrom again, and wherein the implant may be positioned or removed. In one or more embodiments, the one or more barbs may include or be formed as lamellas.

In at least one embodiment, the fixing device and/or the implant surface may include one or more undercuts, wherein the one or more undercuts delimit a cavity that is filled temporarily with a resorbable material. As such, one or more embodiments may allow simple repositioning of the implant, wherein the helical fixing device may be screwed repeatedly into the tissue and removed therefrom again, and wherein the implant may be positioned or removed. In at least one embodiment, the one or more barbs may include or be formed as lamellas.

In one or more embodiments, the helical fixing device may include an outer helix and an inner helix, wherein the inner helix is geometrically discordant with respect to the outer helix such that a clear direction of movement of the inner helix may be predefined. In at least one embodiment, the outer helix may be a guide helix, which allows the inner helix to be screwed into the tissue, and prevents the inner helix from being unscrewed. In one or more embodiments, the outer helix and/or the inner helix may include a sliding coating, at least in regions. The sliding coating eases unscrewing of the outer helix into the implant interior.

In one or more embodiments, the locking device may include one or more spikes, which may be pushed out and which may be extended from the implant surface. In at least one embodiment, the fixing device may be coupled to an actuator, which extends the fixing device from the implant surface. In one or more embodiments, the actuator may move the one or more spikes out from the implant surface simultaneously with the fixing device. In at least one embodiment, the actuator may be rotated in order to move the fixing device and the one or more spikes out from the implant surface. In one or more embodiments, the one or more spikes may, in their end position, simultaneously cause a blocking function with respect to a rotational movement of the actuator.

In at least one embodiment, the fixing device and/or the implant surface may be coated at least in regions with a biocompatible adhesive. In one or more embodiments, the biocompatible adhesive may include at least one of the following substances: fibrin glue and cyanoacrylate adhesive. As such, in one or more embodiments, the implant may be connected to the tissue particularly closely.

BRIEF DESCRIPTION OF THE DRAWINGS

The above and other aspects, features and advantages of at least one embodiment of the invention will be more apparent from the following more particular description thereof, presented in conjunction with the following drawings, wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

One or more embodiments of the invention include securing an implant 100 that has been fastened in the bodily tissue from dislocation, merely using a helix.

At least one embodiment of the invention includes a medical implant that include a helical fixing device to fix the implant in a bodily tissue. In one or more embodiments, the medical implant may include a locking device, wherein after final positioning of the medical implant, before, during or following completion of the screwing of the helix into the bodily tissue, produces a form-fitting and/or force-locked connection to the same bodily tissue. As such, in at least one embodiment, the implant is prevented from being unscrewed. One or more embodiments of the invention may include different locking devices, as will be described hereinafter, that may be used alone or in combination with one another.

Embodiments of the invention will be explained in greater detail hereinafter on the basis of an epicardial pacemaker as the medical implant, however other types of medical implants may be used.

Figure 1:
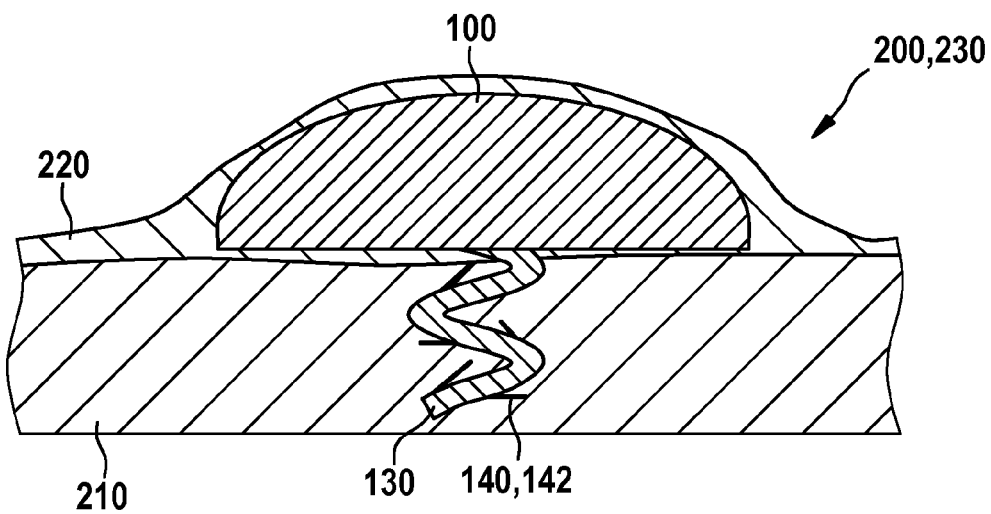
FIG. 1 schematically shows a sectional view of an implant with a helix fixed using barbs according to at least one embodiment of the invention.

FIG. 1 shows a sectional view of an implant 100 that may be inserted into the human and/or animal body 200, according to at least one embodiment of the invention. In one or more embodiments, the implant 100 includes a fixing device 130, wherein the fixing device 130 may be fixed using barbs 142 of a locking device 140, and may be formed as or may include a helix. In at least one embodiment, the implant 100 may be slid at the site of implantation 230 between the myocardium 210 and pericardium 220 and may be fixed in the myocardium 210 using the helix 130. Due to the very violent movements of the pacemaker on the heart muscle, or myocardium, 210 and with respect to the pericardium 220, there is a high likelihood that the screwed fixing device 130 may become unscrewed again over time as a result of these movements and that the implant 100 may be dislodged. In order to prevent this dislocation, by way of one or more embodiments, the fixing device 130 may be provided on its surface with additional barbs 140, such that an unscrewing of the helix 130 is thereby effectively prevented. In at least one embodiment, the implant 100 may be screwed once into the myocardium 210. In one or more embodiments, autonomous detachment of the fixing device 130 may be reliably impeded by the barbs 142.

Figure 2:
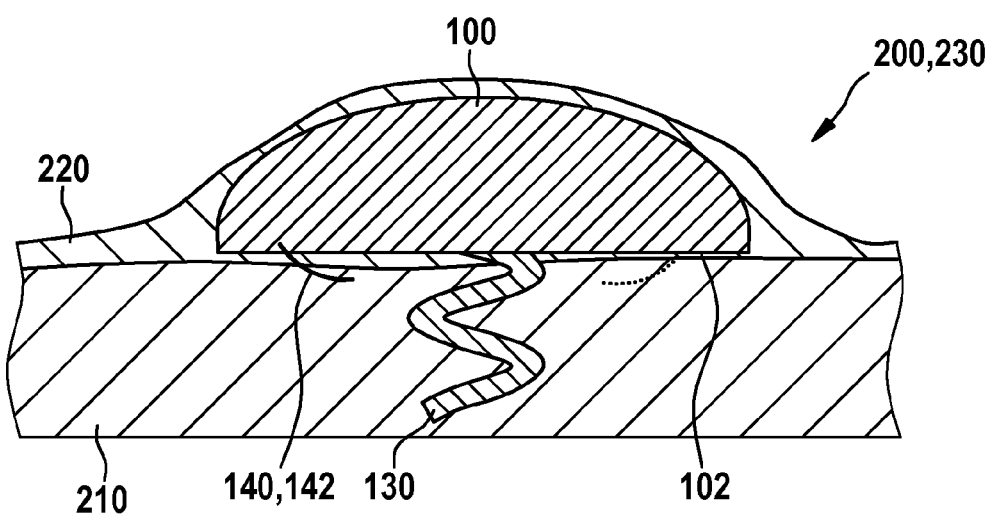
FIG. 2 schematically shows a sectional view of an implant that is fixed using barbs on a housing underside of the implant according to at least one embodiment of the invention.
Figure 3:
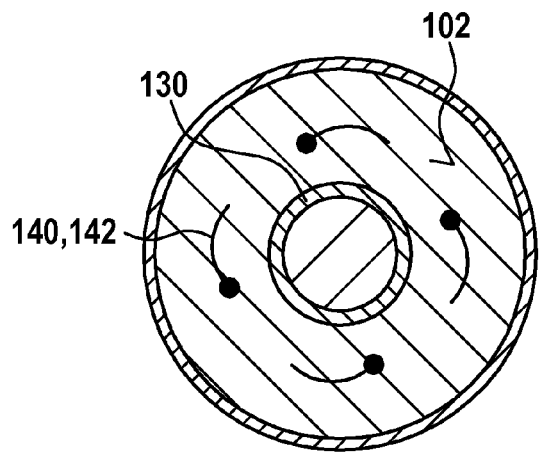
FIG. 3 schematically shows a view of the housing underside of the implant from FIG. 2.

FIG. 2 shows a sectional view of an implant 100 according to at least one embodiment of the invention. As shown in FIG. 2, in one or more embodiments, the implant 100 may be fixed by barbs 142 on an implant surface 102, for example on a housing underside of the implant 100. FIG. 3 shows a view of the housing underside of the implant 100 from FIG. 2, according to at least one embodiment of the invention.

In one or more embodiments, the implant 100 may be slid between the myocardium 210 and the pericardium 220 and may be fixed using a fixing device, such as a helix 130, in the myocardium 210. Due to the very violent movements of the pacemaker on the heart muscle 210 and with respect to the pericardium 220, there is a high likelihood that the screwed helix, such as the fixing device 130, may become unscrewed over time as a result of these movements and that the implant 100 may be dislodged. In order to prevent this dislocation, in at least one embodiment, the barbs 140 may be fitted at the underside of the implant 100 on the implant surface 102 and may be arranged such that the barbs 140 may prevent a rotational movement against the direction in which the helix is screwed in. In one or more embodiments, the barbs 140 may be deployed into the myocardium 210 in the event of such a counter movement and efficiently impede the counter movement.

Figure 4:
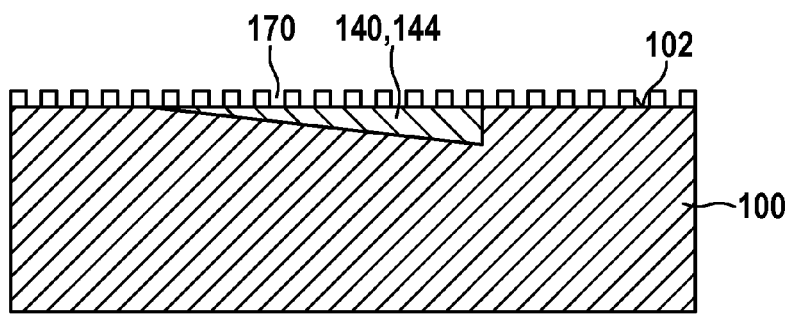
FIG. 4 schematically shows a sectional view of a detail of an implant with barbs according to at least one embodiment of the invention, wherein the barbs are covered by a bioresorbable surface coating.
Figure 5:
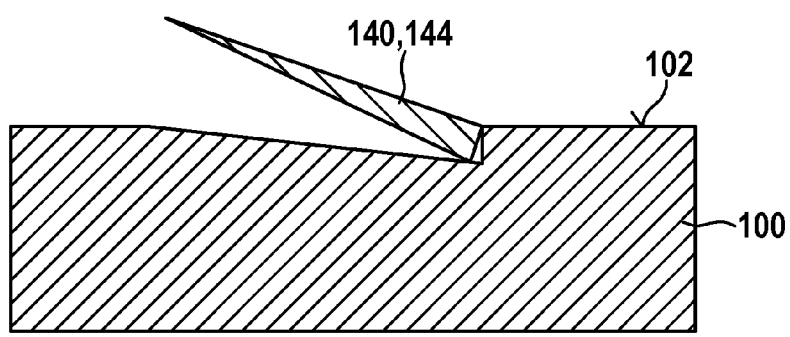
FIG. 5 schematically shows a view of an exposed barb of the implant from FIG. 4.

FIG. 4 shows a sectional view of a detail of an implant 100 including a barb 144 as a locking device 140 according to at least one embodiment of the invention. In one or more embodiments, the barb may be covered by a bioresorbable coating 170 on an implant surface 102. Such barbs 144, in at least one embodiment, may be provided on the fixing device. FIG. 5 shows a view of an exposed barb 144 of the implant 100 from FIG. 4, according to at least one embodiment of the invention.

In one or more embodiments, the barb 144 may be covered by the bioresorbable surface coating 170 during the insertion of the implant 100, such that the implant 100 may be positioned. In at least one embodiment, only when the bioresorbable coating 170 has dissolved, the barbs 144 may be deployed by a spring force and may protrude into the tissue, wherein the barbs 144 may form an effective anti-twist mechanism.

According to one or more embodiments, the barbs 144 may include materials such as, for example, one or more of nitinol, high-grade steel, platinum, titanium and PEEK polymers.

Figure 6:
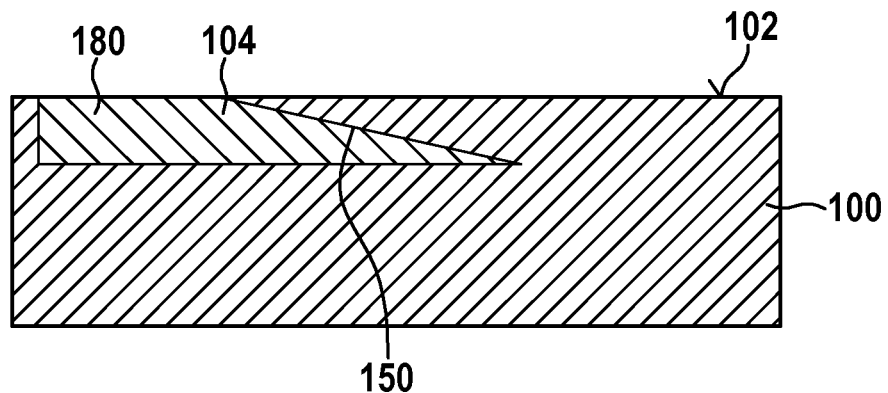
FIG. 6 schematically shows a sectional view of a detail of an implant with barbs according to at least one embodiment of the invention, wherein the barbs are integrated in a surface and surrounded in part by bioresorbable material.
Figure 7:
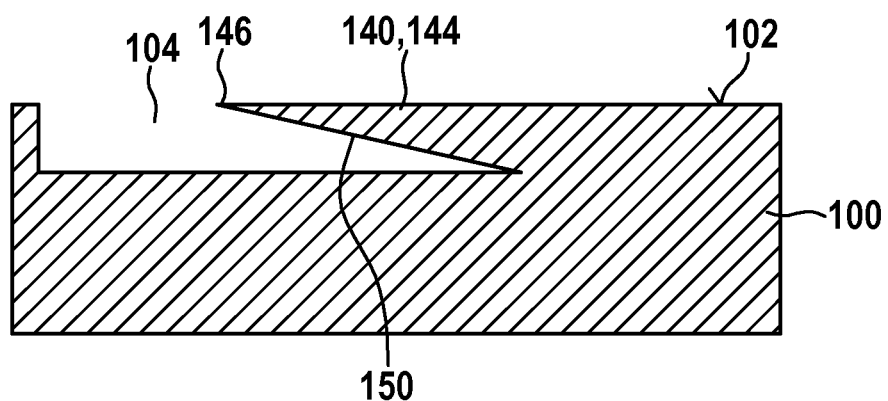
FIG. 7 schematically shows a view of an exposed barb of the implant from FIG. 6.

FIG. 6 shows a sectional view of a detail of an implant 100 according to at least one embodiment of the invention. As shown in FIG. 4, one or more embodiments may include a barb 144 as a locking device 140, which may be integrated as an undercut 150 into a surface and may be surrounded in part by a bioresorbable material. FIG. 7 shows a view of an exposed barb 144 of the implant 100 from FIG. 6, according to at least one embodiment of the invention.

One or more embodiments of the invention may include one or more undercuts 150 on the fixing device 130 and/or on the implant surface 102. In at least one embodiment, the undercut 150 may delimit a cavity 104 on the surface, which may be filled temporarily with a resorbable material 180.

As soon as the filling formed from resorbable material 180 has dissolved, by way of at least one embodiment, the barb may hook into the tissue in the event of an undesirable rotational movement, which may lead to the detachment of the helix from the tissue, since a sharp edge 146 of the barb is now effective.

In one or more embodiments, as shown in FIGS. 4 to 7, the position of the implant 100 during the implantation may initially still be corrected and the actual safeguarding against dislocation is only effective later. In at least one embodiment, a coating 170 or covering/filling 180 may be used, optionally, which starts the dissolution process of the coating or filling using an external trigger, for example a selective energy input. In one or more embodiments, the barbs 144 may be formed on the implant surface 102, for example as a lamella structure.

In at least one embodiment of the invention, the fixing device 130 may include an outer helix and an inner helix, wherein the inner helix is geometrically discordant with respect to the outer helix such that a clear preferred direction of movement of the inner helix may be predefined. In one or more embodiments, the inner helix may be screwed from the outer helix into the tissue and may fix the implant 100. In at least one embodiment, an unscrewing of the inner helix may be impeded by shape deviations, distortions and the like. In one or more embodiments, the outer helix and/or the inner helix may optionally include a sliding coating, at least in regions, such that an unscrewing of the outer helix is facilitated. In at least one embodiment, the outer helix may form or include a guide helix for the inner helix and may hold the inner helix initially in a form necessary to screw into the tissue.

Figure 8:
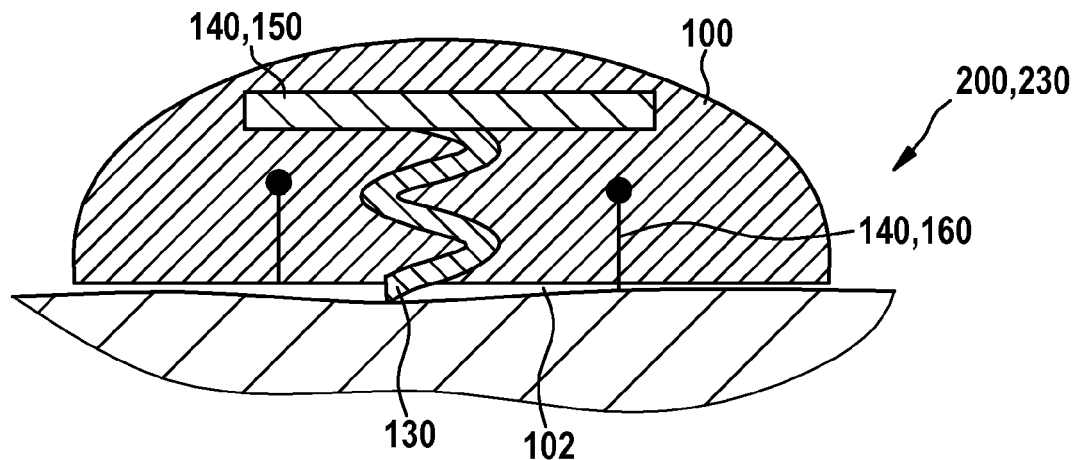
FIG. 8 schematically shows a sectional view of an implant with a helix fixed using spikes which may be pushed out, wherein the helix is in the retracted state, according to at least one embodiment of the invention.
Figure 9:
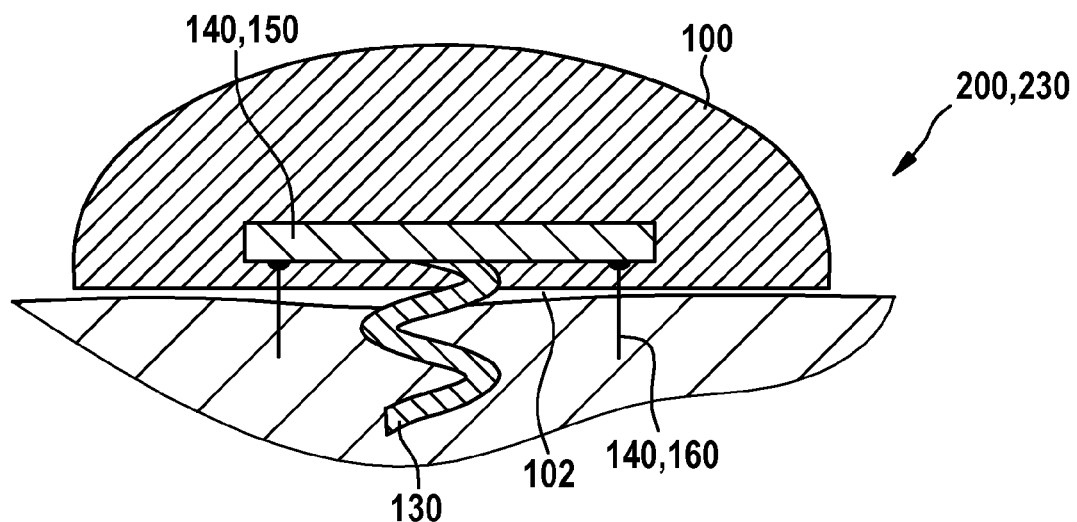
FIG. 9 schematically shows a sectional view of the implant from FIG. 8 fixed using spikes that have been pushed out.

FIGS. 8 and 9 illustrate a sectional view of the implant according to at least one embodiment of the invention. As shown in FIGS. 8 and 9, in one or more embodiments, the implant 100 may be fixed using spikes 160 of a locking device 140, wherein the spikes 160 may be pushed out. By way of at least one embodiment, FIG. 8 shows the implant 100 with a fixing device, such as a helix 130, in a retracted state, and FIG. 9 shows the implant 100 from FIG. 8 fixed using spikes 160 that have been pushed out.

In one or more embodiments, the implant 100 includes a helix that may be unscrewed from the implant housing in order to fix the implant 100 in the tissue of a body 200. In at least one embodiment, the fixing device 130 may be formed such that it includes an accordingly dimensioned actuator 150 and one or more extendible spikes 160. In one or more embodiments, the actuator 150 may be activated, for example, using a suitable actuation device. In at least one embodiment, in the screwed-in state, the spikes 160 may be withdrawn into the housing of the implant 100. According to one or more embodiments, if the fixing device, such as a helix 130, is completely unscrewed, the spikes 160 may be slid out by the actuator 150 such that the spikes 160 produce an anti-twist mechanism via contact with the bodily tissue. At least one embodiment of the invention may include a blocking function, wherein the rotation of the actuator 150 is blocked by the spikes 160 latching into the actuator 150 when the spikes 160 are in their end position.

In one or more embodiments, the fixing device 130 and/or the implant surface 102 may be coated at least in regions with a biocompatible adhesive. In at least one embodiment, the biocompatible adhesive may include at least a fibrin glue and/or a cyanoacrylate adhesive.

One or more embodiments may include a coating, which is accessible to the adhesive, such as a primer, on the implant side. In at least one embodiment, the materials for primers may include, for example, one or more of solutions of the aromatic carboxylic acids benzoic acid and salicylic acid in acetone, acetic acid-based primers and alternative biocompatible self-etching primers.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A medical implant configured to be inserted into the human and/or animal body, comprising:
    a helical fixing device that fixes the medical implant at a site of implantation;
    a locking device that impedes an autonomous detachment of the helical fixing device from the site of implantation;
    an implant surface; and,
    a resorbable coating on the implant surface;
    wherein the locking device is one or more of coupled to the helical fixing device and coupled to the implant surface,
    wherein the locking device comprises one or more barbs on the helical fixing device,
    wherein at least one barb of the one or more barbs is covered temporarily by the resorbable coating,
    wherein the at least one barb comprises a spring force, and
    wherein when the resorbable coating that is on the implant surface and that covers the at least one barb has dissolved, then the at least one barb
        is deployed by the spring force,
        forms an anti-twist mechanism, and
        protrudes out from under the implant surface into the site of implantation to fix the medical implant at the site of implantation.

2. The medical implant as claimed in claim 1, wherein the locking device further comprises one or more barbs on the implant surface.

3. The medical implant as claimed in claim 1, wherein the resorbable coating fixes the at least one barb on one or more of the helical fixing device and the implant surface against the spring force of said at least one barb.

4. The medical implant as claimed in claim 1, wherein one or more of the helical fixing device and the implant surface comprise one or more undercuts, wherein the one or more undercuts delimit one or more cavities, wherein the one or more cavities are temporarily filled with a resorbable material.

5. The medical implant as claimed in claim 1, wherein the helical fixing device comprises an outer helix and an inner helix, wherein the inner helix is geometrically discordant with respect to the outer helix, such that a direction of movement of the inner helix is predefined.

6. The medical implant as claimed in claim 5, wherein one or more of the outer helix and the inner helix comprise a sliding coating at least in regions.

7. The medical implant as claimed in claim 1, wherein the locking device further comprises one or more spikes, wherein the one or more spikes are pushed out and are extended from the implant surface.

8. The medical implant as claimed in claim 7, wherein the helical fixing device is coupled to an actuator, and wherein the actuator extends the helical fixing device from the implant surface.

9. The medical implant as claimed in claim 8, wherein the actuator extends the one or more spikes from the implant surface simultaneously with the helical fixing device.

10. The medical implant as claimed in claim 1, wherein one or more of the helical fixing device and the implant surface are coated at least in regions with a biocompatible adhesive.

11. The medical implant as claimed in claim 10, wherein the biocompatible adhesive comprises at least one of fibrin glue and cyanoacrylate adhesive.

12. The medical implant as claimed in claim 1, wherein the implant surface comprises a flat surface, such that when the at least one barb protrudes out from under the implant surface into the site of implantation the at least one barb protrudes out from the flat surface.

13. A medical implant configured to be inserted into the human and/or animal body, comprising:
    a helical fixing device that fixes the medical implant at a site of implantation;
    a locking device that impedes an autonomous detachment of the helical fixing device from the site of implantation;
    an implant surface, wherein the implant surface comprises a flat surface; and,
    a resorbable coating on the implant surface;
    wherein the locking device is one or more of coupled to the helical fixing device and coupled to the implant surface,
    wherein the locking device comprises one or more barbs on the helical fixing device,
    wherein at least one barb of the one or more barbs is covered temporarily by the resorbable coating,
    wherein the at least one barb comprises a spring force,
    wherein when the resorbable coating that is on the implant surface and that covers the at least one barb has dissolved, then the at least one barb
    is deployed by the spring force,
    forms an anti-twist mechanism, and
    protrudes out from under the implant surface into the site of implantation to fix the medical implant at the site of implantation, such the at least one barb protrudes out from the flat surface, and
    wherein the locking device further comprises one or more spikes, wherein the one or more spikes are pushed out and are extended from the implant surface.

* * * * *